United States Patent
Knisley

[11] Patent Number: 5,995,871
[45] Date of Patent: Nov. 30, 1999

[54] SYSTEM AND METHOD FOR CARDIOVERSION USING SCAN STIMULATION

[75] Inventor: Stephen B. Knisley, Vestavia Hills, Ala.

[73] Assignee: UAB Research Foundation, Birmingham, Ala.

[21] Appl. No.: 08/960,448

[22] Filed: Oct. 29, 1997

[51] Int. Cl.[6] .................................................. A61N 1/368
[52] U.S. Cl. .............................................. 607/15; 607/14
[58] Field of Search .................... 607/5, 9, 15, 14

[56] References Cited

U.S. PATENT DOCUMENTS

| | | |
|---|---|---|
| 4,030,509 | 6/1977 | Heilman et al. . |
| 4,136,702 | 1/1979 | Trabucco . |
| 4,574,814 | 3/1986 | Buffet . |
| 4,628,937 | 12/1986 | Hess et al. . |
| 4,641,656 | 2/1987 | Smits . |
| 4,708,145 | 11/1987 | Tacker, Jr. et al. . |
| 4,969,463 | 11/1990 | Dahl et al. . |
| 5,010,894 | 4/1991 | Edhag . |
| 5,050,601 | 9/1991 | Kupersmith et al. . |
| 5,103,822 | 4/1992 | Duncan . |
| 5,181,511 | 1/1993 | Nickolls et al. . |
| 5,224,476 | 7/1993 | Ideker et al. .................... 607/9 |
| 5,230,337 | 7/1993 | Dahl et al. . |
| 5,282,845 | 2/1994 | Bush et al. . |
| 5,327,909 | 7/1994 | Kiser et al. . |
| 5,342,407 | 8/1994 | Dahl et al. . |
| 5,360,442 | 11/1994 | Dahl et al. . |
| 5,376,105 | 12/1994 | Hedberg . |
| 5,405,374 | 4/1995 | Stein . |
| 5,411,527 | 5/1995 | Alt . |
| 5,423,864 | 6/1995 | Ljungstroem . |
| 5,425,364 | 6/1995 | Imran . |
| 5,433,729 | 7/1995 | Adams et al. . |
| 5,439,485 | 8/1995 | Mar et al. . |
| 5,456,254 | 10/1995 | Pietroski et al. . |
| 5,468,254 | 11/1995 | Hahn et al. .................... 607/5 |
| 5,489,293 | 2/1996 | Pless et al. . |
| 5,514,164 | 5/1996 | Mann et al. .................... 607/25 |
| 5,584,865 | 12/1996 | Hirschberg et al. . |

OTHER PUBLICATIONS

Knisley S. Davis C. "Membrane Polarization During Point Stimulation in Perfused Rabbit Hearts," Circulation 90; I–176:1994. (abstract).

Knisley S., Hill B., Ideker R., "Virtual Electrode Effects in Myocardial Fibers," Biophysical Journal 66;719–728: 1994.

Saypol J., Roth B., "A Mechanism for Anisotropic Reentry in Electrically Active Tissue" Biomedical Engineering and Instrumentation Program, National Center for Reserch Resources, Nat'l Institute of Health, Bethesda, Maryland.

Wikswo J., Lin S., Abbas R., "Virtual Electrodes in Cardiac Tissue: A Common Mechanism for Anodal and Cathodal Stimulation" Biophysical Journal 69:2195–2210: 1995.

Knisley S., "Transmembrane Voltage Changes During Unipolar Stimulation of Rabbit Ventricle" Div. of Cardiovascular Disease of the School of Medicine and Dept. of Biomedical Engineering, University of Alabama Birmingham. accepted Aug. 27, 1995.

(List continued on next page.)

Primary Examiner—William E. Kamm
Assistant Examiner—Carl H. Layno
Attorney, Agent, or Firm—Gifford, Krass, Groh, Sprinkle, Anderson & Citkowski, P.C.

[57] ABSTRACT

A method and system for applying therapeutic electrical pulses to the heart includes a plurality of spaced apart electrodes. Each electrode in electrical communication with a pulse generator and are operative to deliver at least one energy pulse to a patient's heart. Sensors and electrical communication with a controller are operative to detect an abnormal rhythm in the patient's heart and transmit a signal to a controller to indicate an abnormal rhythmic condition. The controller is configured to receive the abnormal rhythmic signal from the sensor and cause the pulse generator to emit a sequence of spatially and temporally distinct pulses through the electrodes, each pulse passing through at least one of the electrodes.

28 Claims, 3 Drawing Sheets

OTHER PUBLICATIONS

Knisley S., Grant A., "Asymmetrical Electrically Induced Injury of Rabbit Ventricular Myocytes", J Mol Cell Cardiol 27, 1111–22 (1995).

Knisley S., Smith W., Ideker R., "Prolongation and Shortening of Action Potentials By Electrical Shocks in Frog Ventricular Muscle", AM.J.Physiol.266 (Heart Circ. Physiol. 35) H2348–H2358, 1994.

Bourland J.D., Tacker, Jr. W.A., Wessale J.L., Kallok M.J., Graf J.E., Geddes L.A., "Sequential Pulse Defibrillation for Implantable Defibrillators" Biomedical Engineering Center, Purdue University, West Lafayette, Indiana and †Medtronic, Inc., Minneapolis, Minnesota.

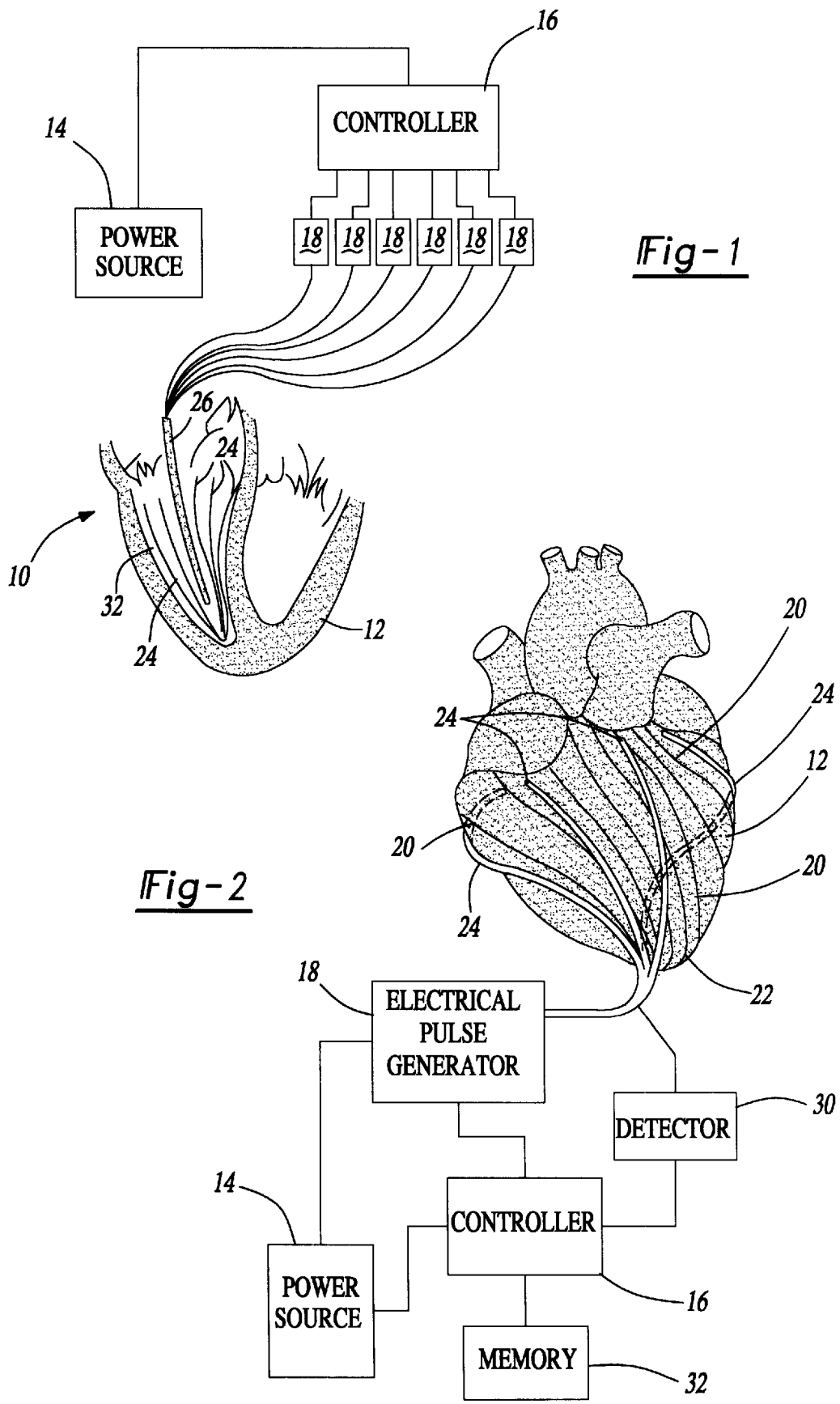

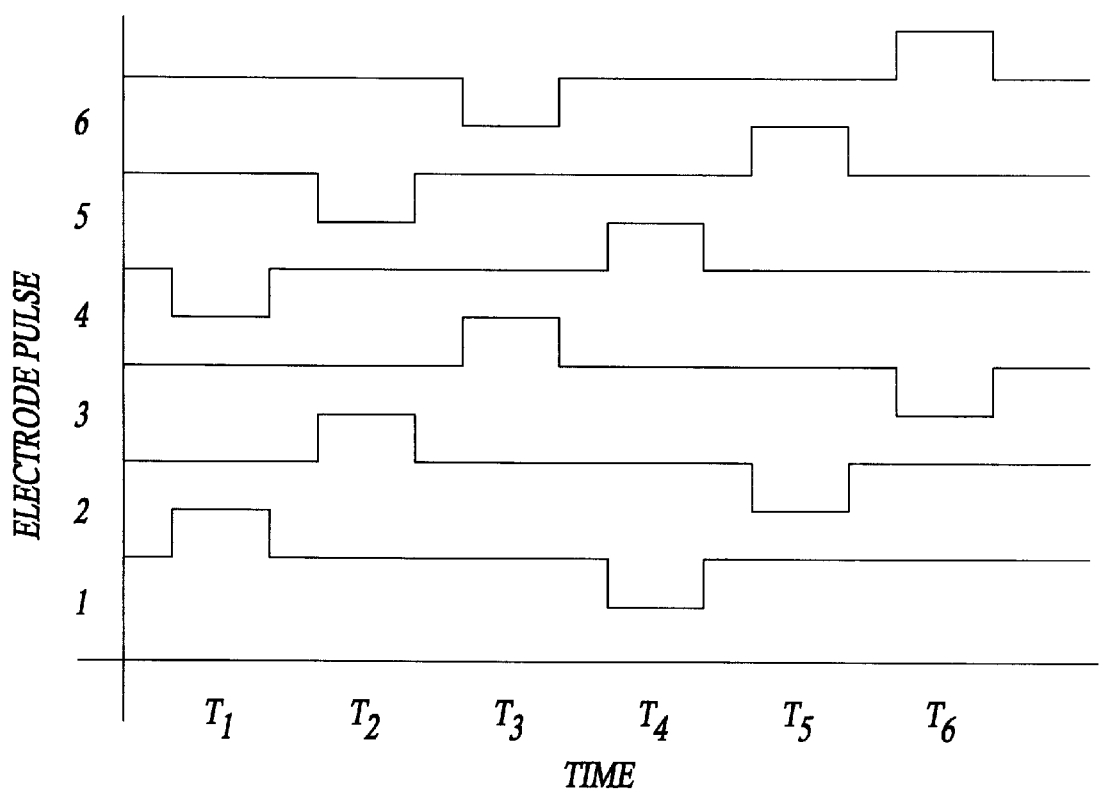
Fig-5
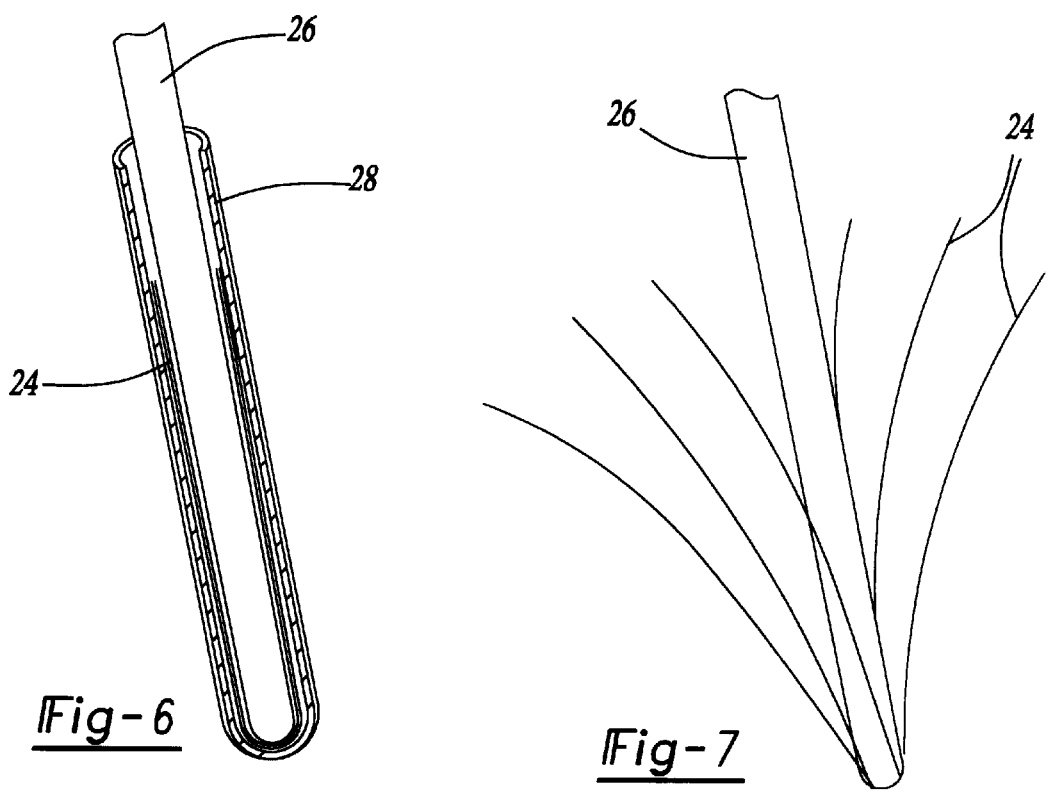
Fig-6
Fig-7

SYSTEM AND METHOD FOR CARDIOVERSION USING SCAN STIMULATION

FIELD OF THE INVENTION

The present invention relates generally to a system and method for terminating a cardiac arrhythmia or fibrillation by applying therapeutic electrical pulses to the heart, and more particularly to such a method and system utilizing scan stimulation whereby temporally and spatially distinct electrical pulses are applied to a heart.

BACKGROUND OF THE INVENTION

A variety of physiological conditions exist where irregular electrical activity of a heart results in an abnormal heartbeat. To correct the abnormal heartbeat, a multiplicity of systems and methods have been developed whereby at least one therapeutic electrical shock or pulse is applied to the heart through one or two electrodes to disrupt the irregular electrical activity so that the heart may revert to its regular electrical activity, resulting in a normal heartbeat.

Such systems and methods utilize electrical field stimulation wherein a sufficiently large shock is applied to the heart through one or two electrodes to produce a desired extracellular potential gradient in large regions of the heart distant from the electrodes. In this manner, the irregular electrical activity throughout the heart is sufficiently disrupted to permit restoration of normal electrical activity and normal heartbeat.

Many prior art systems and methods first detect, through a variety of known devices, a rhythmic condition such as tachycardia (relatively rapid heart action), arrhythmia (an alteration in the rhythm of the heartbeat either in time or force), tachyarrhythmia (arrhythmia characterized by a rapid, irregular heartbeat), and atrial or ventricular fibrillation (very rapid uncoordinated constrictions of the atria or ventricle, respectively, resulting in loss of the ability to pump blood, most particularly in the case of ventricular fibrillation). Next, an electrical shock is applied to the heart through one or two electrodes positioned on or within the heart. The electrical shock applied to the heart through the electrodes is large enough to produce an electric field in regions of the heart near and remote from the electrodes. Selected prior art systems include feedback mechanisms whereby the electrical condition of the heart is detected subsequent to the application of the first shock and, if a normal heart rhythm is not restored, an additional electrical shock is applied to the heart.

Measurements have recently been obtained utilizing optical mapping techniques with voltage-sensitive fluorescent dyes in hearts which indicate that the effects of an electrical stimulation pulse on the transmembrane potential of heart cells are greatest in the region within one millimeter of the stimulation electrode.

Because the strength of an electric field decreases with increasing distance from the electrodes, a pulse which produces an electric field sufficient for defibrillation in a region remote from an electrode will produce a much stronger electric field near the electrode. Injuries are produced in heart cells by such strong electrical stimulation when, during the electrical pulse, the transmembrane potential exceeds the threshold for cell membrane electroporation. As prior art cardioversion and defibrillation systems require the application of high voltage pulses to the heart to produce an electric field in regions of the heart remote from the electrodes, such systems also have large energy requirements.

One method, disclosed in U.S. Pat. No. 4,708,145 to Tacker, Jr. et al. attempts to avoid areas of high current density in the heart by using a sequential pulse, multiple pathway defibrillation method for controlling ventricular fibrillation and tachyarrhythmias. A catheter carrying a first and second electrode is located in the right ventricle and a third electrode is located either at the chest wall or at the abdominal cavity. The second and third electrodes are sequentially paired and pulsed with the first electrode to control ventricular fibrillation and other tachyarrhythmias. While the Tacker, Jr. et al device applies shocks to the heart through spaced apart electrodes, these shocks are intended to traverse the heart through particular pathways to establish a sufficient electric field in regions of the heart remote from the electrodes.

Since the effects of electrical shocks on transmembrane potentials are large near an electrode, a system to produce effects primarily in the cells near an electrode could require stimulation voltage or current that is less than the voltage or current needed to produce a desired electric field remote from an electrode. Such a system would require low current pulses which could decrease both the system energy requirements and cellular damage resulting from each electrical pulse. Low strength stimulation at a single site is already known to effect arrhythmias and even, as reported by Salama, halt ventricular tachycardia in isolated rapid hearts when applied to Purkinje fibers which occur on the endocardium.

Although the prior art provides a variety of cardioversion and defibrillation methods and systems, there remains a need for a method and system for cardioversion of a heart which utilizes low voltage pulses which minimizes damage to the heart with low power requirements.

SUMMARY OF THE INVENTION

The present invention is intended to produce effects on transmembrane potentials in the cells of the heart fiber proximate to each of a plurality of spaced apart electrodes rather than utilizing high energy pulses applied through one or two electrodes to produce a desired electric field in cells positioned away from an electrode. An abnormal rhythmic pattern of a heart is disrupted by the application of therapeutic electrical pulses through a plurality of spaced apart electrodes, resulting in stimulation of a sufficient number of cells. The present invention thus requires less stimulation voltage or current than conventional devices which produce an electric field remote from the electrodes, thereby decreasing both the energy requirements of the cardioverter or defibrillator and cellular damage to the heart.

The system of the present invention for applying therapeutic electrical pulses to a patient's heart includes a power source and a controller in electrical communication with the power source. A pulse generator, in electrical communication with the controller, is configured to generate a sequence of energy pulses. A plurality of spaced apart electrodes are provided, each electrode being in electrical communication with the pulse generator. Each electrode is configured to deliver an energy pulse generated by the pulse generator to the patient's heart. The controller is operative to cause the pulse means to direct, through the electrodes, a sequence of spatially and temporally distinct pulses to the heart.

Preferably, detecting means are provided which are in electrical communication with the controller. The detecting means are operative to detect an abnormal rhythm in a patient's heart and transmit a signal to the controller to indicate an abnormal rhythmic condition. In selected embodiments, the electrodes may be operative to detect electrical activation of heart fibers proximate to each such electrode. The controller is operative to receive the signal indicating an abnormal rhythmic condition and to cause the pulse means to direct, through the electrodes, a sequence of spatially and temporally distinct pulses to the patient's heart, each pulse passing through at least one of the electrodes.

The method for applying therapeutic electrical pulses to the heart comprises the steps of providing a plurality of spaced apart electrodes, each electrode in electrical communication with heart fibers adjacent to such electrode. Preferably, an abnormal cardiac rhythmic condition such as fibrillation, tachycardia, tachyarrhythmias or the like is detected through detectors or sensors in contact with the heart. A sequence of spatially and temporally distinct pulses are directed to the heart, each pulse applied to the heart through at least one of the plurality of electrodes. In the preferred embodiment, a first pulse is directed to the heart to a first electrode at a time T1 and a second pulse is directed to the heart through a second electrode at time T2, time T2 being later in time than T1.

Preferably, at least one of the electrodes is elongated and extends parallel to an elongated fiber of the heart which is positioned proximate to such electrode.

A wide variety of stimulation sequences may be utilized in the present invention, such as pairing a first and third electrode so that a first pulse is directed to the heart through a first electrode at time T1 and a third pulse is simultaneously directed to the heart through a third electrode at T1. In such an embodiment, a second pulse may be directed to the heart through a second electrode at time T2 and a fourth pulse may be directed to the heart through a fourth electrode at a time T2. In any of the embodiments of the present invention, the pulses sequentially directed to the heart may have the same or opposite polarity.

The method may also include the step of storing the sequences of spatially and temporally distinct pulses which have been directed to the heart.

In the system of the present invention the controller may be operative to receive a first signal pattern from the detector or sensor, the first signal pattern being indicative of a first heart rhythm. The controller is further operative to determine if therapeutic electrical pulses are to be applied to the heart. Preferably, this step includes the step of sending the received signal pattern to an artificial neural network configured to recognize a signal pattern indicative of an abnormal heart rhythm. The controller is also preferably operative to receive from the artificial neural network a signal indicating if therapeutic electrical pulses are to be applied to the heart.

In alternate embodiments, the step of determining if therapeutic electrical pulses are to be applied to the heart may include the steps of comparing the received signal pattern with at least one stored pattern indicative of acceptable heart rhythms. If the received signal pattern is comparable to at least one stored pattern indicative of an acceptable heart rhythm, therapeutic electrical pulses are not to be directed to the heart. If the received signal pattern is not comparable to a stored pattern indicative of an acceptable heart rhythm, therapeutic electrical pulses are to be directed to the heart.

If therapeutic electrical pulses are to be applied to the heart, the controller is operative thereafter to generate a first control signal and direct the first control signal to the pulse generator to cause the pulse generator to apply a first pattern of temporally and spatially separated pulses to the plurality of electrodes. The controller is further configured to receive a second signal pattern from the sensor means, the second signal pattern being indicative of a second heart rhythm. The controller is then configured to determine if therapeutic electrical pulses are to be applied to the heart using the steps discussed supra. If therapeutic electrical pulses are to be applied to the heart, the controller is configured to generate a second control signal and direct the second control signal to the pulse generator to cause the pulse generator to apply a second pattern of temporally and spatially separated pulses to the plurality of electrodes. If therapeutic electrical pulses are not to be applied to the heart, the second control signal is stored in association with the second signal pattern.

Other objects, advantages and applications of the present invention will be made clear by the following detailed description of a preferred embodiment of the present invention. The description makes reference to drawing in which:

BRIEF DESCRIPTION OF THE DRAWINGS

FIG. 1 is a view of an embodiment of the present invention wherein the electrodes have been transvenously inserted into the heart;

FIG. 2 is a view of an alternate embodiment of the present invention wherein the electrodes have been applied to the exterior of the heart beneath or upon the pericardium;

FIG. 5 is yet another graphical representation of a sequence of electrode pulses over time;

FIG. 6 is a view of the catheter of the present invention corresponding to the embodiment of FIG. 1 during transvenous insertion; and FIG. 7 is a view of the catheter with electrodes of the present invention corresponding to the embodiment of FIG. 1 in their respective positions after transvenous insertion.

DETAILED DESCRIPTION

Figure 3:
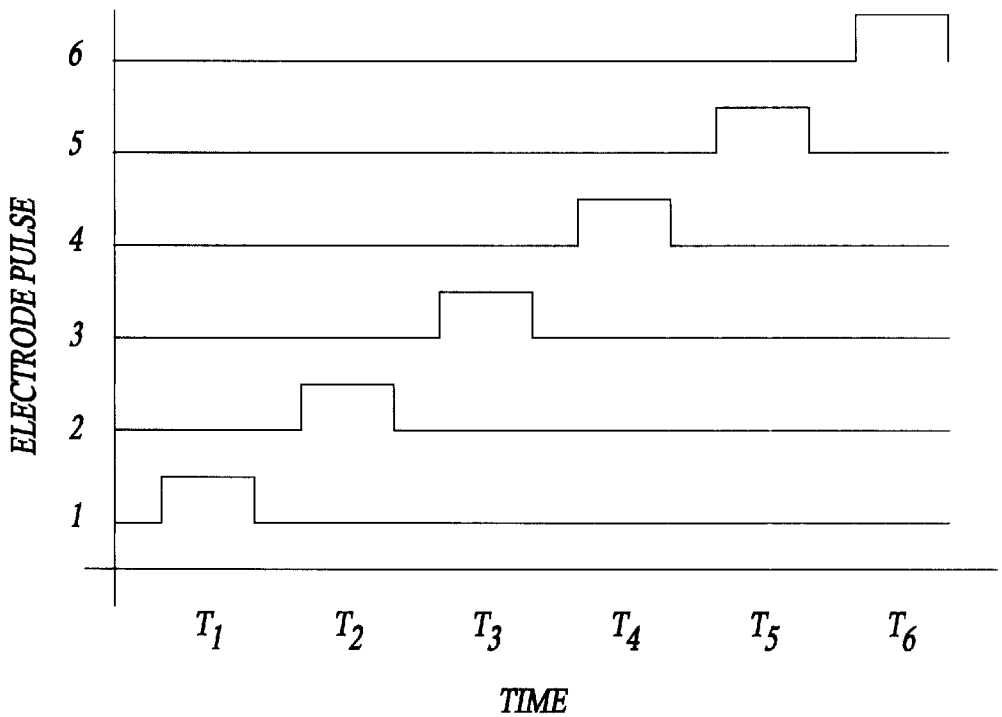
FIG. 3 is a graphical representation of a sequence of electrode pulses over time.

As shown in FIG. 1, an implantable embodiment of the present invention includes a plurality of spaced apart electrodes 24 preferably positioned within the right ventricle 32 of the heart 12. Each electrode 24 is operative to deliver an energy pulse generated by a pulse generator 18 to the patient's heart. Each electrode may be in electrical communication with a discrete pulse generator 18, or a single pulse generator 18 may be in electrical communication with all or a subset of the electrodes 24, such pulse generator being operative to selectively direct a pulse through each electrode.

In the preferred embodiment, at least four and preferably six electrodes are utilized, although more or less may be successfully utilized in the present invention. The electrodes may also be arranged to contact the heart in any of a variety of ways, including a preformed "sock" of spaced electrodes which envelop the heart. The electrodes may be positioned anywhere in or on the heart.

In FIGS. 6 and 7, a preferred embodiment of the electrodes 24 is shown therein, the electrodes emanating from a single point at the lower end of a catheter 26. For transvenous insertion of the electrodes of the present invention, a sheath 28 may be placed over the electrodes 24 during insertion into the heart 12. Once the electrodes 24 and catheter 26 have been inserted into the proper cavity of the heart, the sheath 28 may be removed from the heart 12, thereby allowing the electrodes 24 to fan out and lie against the heart fibers. The electrode arrangement depicted in FIGS. 6 and 7 may be removed from the heart by sliding the sheath 28 over the catheter 26 and, by withdrawing the catheter 26 out of the heart cavity, flexible electrodes 24 are gradually drawn into sheath 28.

Preferably, each electrode is elongated and of the type described in U.S. Pat. No. 5,824,028, entitled Line Electrode Oriented Relative to Fiber Direction, which is incorporated herein by reference. Each electrode 24 is preferably configured to lie in a direction parallel to an adjacent heart fiber. The utilization of an elongated electrode which is configured to lie parallel to an elongated fiber of the heart provides particular advantages to any cardioversion system, as low power energy pulses applied to the heart through such particularly positioned electrodes reduces the spatial variation of transmembrane voltages in cells proximate to the electrodes, and minimizes the likelihood of inducing arrhythmic activity such as that described by Saypol for point stimulation. Such particularly positioned electrodes may lessen damage to heart cells proximate to such electrodes.

In the preferred embodiment of FIG. 1, a controller 16, in electrical communication with a power source 14, is operative to cause the pulse generator to direct a sequence of spatially and temporally distinct pulses to the heart 12 through the spaced apart electrodes 24, each pulse passing through at least one of the electrodes 24. The controller 16 may be operative to cause each of a plurality of pulse generators 18 to direct an energy pulse through the electrode 24 in electrical communication with each pulse generator so that a sequence of temporally distinct pulses is directed through the spaced apart electrodes. Alternately, the controller may be configured to cause the pulse generator to direct a series of pulses through the plurality of electrodes in electrical communication with the pulse generator 18. Such a series of pulses or "scan" is intended to disrupt the abnormal heart rhythm and reestablish normal heart rhythm in the patient.

Scan stimulation of a heart may occur in a random pattern wherein the spaced apart electrodes 24 are randomly pulsed, or a predetermined pattern wherein the electrodes are pulsed in a clockwise or counter-clockwise sequence around the heart. Alternatively, a scan pattern could first stimulate an endocardial electrode positioned near the heart apex and scan on the endocardium of ventricular walls towards the base of the heart, thus mimicking the propagation of electrical impulses from the Purkinje fibers that excite the ventricular walls in normal heart rhythm. Stimulation patterns could be particularly configured to increase the effectiveness of the ventricular or atrial defibrillation or cardioversion. The sequence of scan stimulation may vary considerably and is preferably customized to the rhythmic abnormality.

Figure 4:
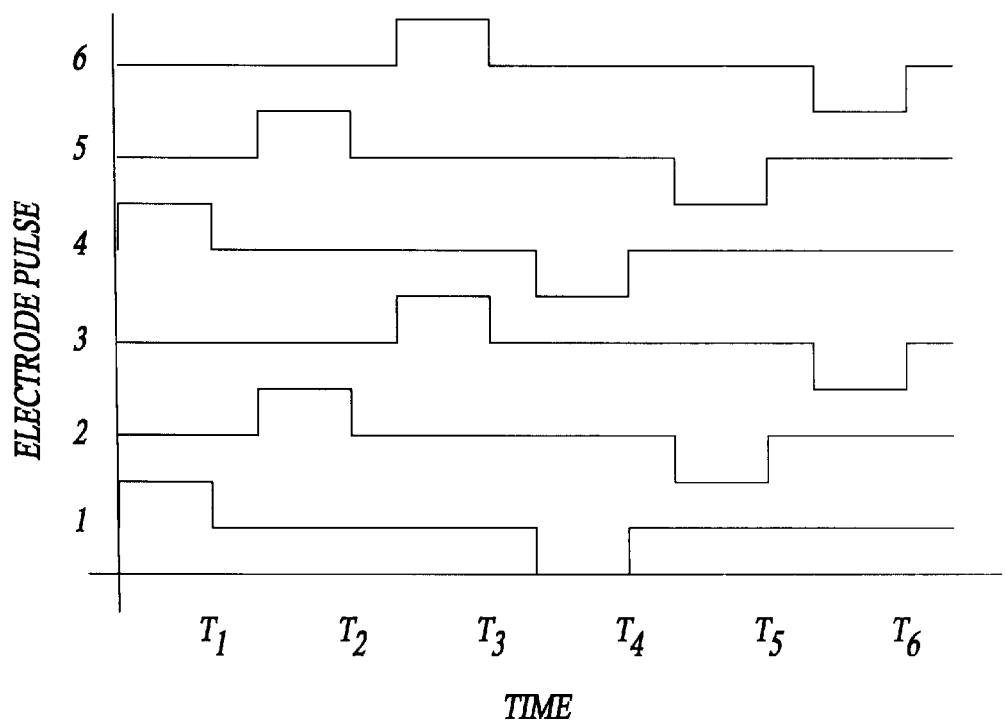
FIG. 4 is an alternate graphical representation of a sequence of electric pulses over time.

FIGS. 3, 4 and 5 depict stimulation sequences which may be applied to the heart. Unipolar or bipolar stimulation may be applied through the electrodes 24. The electrodes may be "paired" so that, at a given time T, two of the spaced apart electrodes direct energy pulses simultaneously to the heart. Such pulses may be of the same or opposite polarity. The controller 16 and pulse generators 18 may be configured so that the scan can be performed with different polarities and different electrodes at different times so that hyperpolarization and depolarization occur in cells near each electrode. Since each electrode may deliver a stimulation occurring at a different time during a scan, the effects of such pulses on cells at numerous locations in the heart could produce ventricular or atrial defibrillation or cardioversion.

FIG. 2 depicts an embodiment of the present invention wherein electrodes 24 are positioned on the epicardium of the heart, such electrodes being preferably aligned with the elongated fibers 20 of the heart 12. An electrical pulse generator 18 is in electrical communication with a controller 16 and the electrodes 24. The controller 16 is in electrical communication with a detector 30 which is configured to sense myocardial activations, thus detecting an abnormal rhythmic condition in the patient's heart such as atrial or ventricular fibrillation, tachyarrhythmia, or arrhythmia. Myocardial activations could be sensed at the electrodes 24 and transmitted to controller 16, the electrodes thus functioning as sensors or detectors. Alternately, separate sensors may be utilized.

Upon detection of an abnormal rhythmic condition in the heart 12, the detector 30 transmits a signal which is indicative of the abnormal rhythmic condition to the controller 16. The detector 30 may be configured to send a particular signal which is indicative of ventricular fibrillation, atrial fibrillations, tachyarrhythmia or the like to the controller 16. The controller 16 is operative to receive such signal and cause the pulse generator 18 to direct an appropriate sequence of temporally and spatially distinct pulses through the spaced apart electrodes. In a preferred embodiment, scan sequences are configured to terminate the particular rhythmic abnormality detected. Such sensing and control of stimulation could be performed with digital and/or analog processing circuitry which could operate in real time with low energy in an implantable device.

Additionally, the controller may include or be in electrical communication with a memory 32. Upon detection of an abnormal rhythmic condition, the controller 16 may be configured to retrieve from a predetermined location in the memory 32 the appropriate scan stimulation sequence to terminate such an abnormal rhythmic condition. The controller may alter the scan sequence at any time to accommodate rhythmic or other changes detected in the heart. Memory 32 may also store previously detected abnormal rhythmic conditions as well as the sequence of temporally and spatially distinct pulses which terminated such abnormal rhythmic condition. Additionally, the controller may be operative to perform data base functions such as sorting, selecting and the like on the information stored in memory 32 to determine the most effective and safest way to restore a normal rhythm to the heart. The controller may use the information stored in memory in combination with a program or the like to create a new sequence of pulses to be applied to the heart as well as to determine the most effective scan sequence for the patient, store that sequence and change its program to utilize that successful sequence in future defibrillation episodes.

At implantation in patients, the stimulation electrodes 24 could also be used as recording electrodes to map the arrhythmia or other condition by connecting the signals to an external recording system or memory 32. Also, internal memory storage and readout of stored recordings could be performed by physicians after implantation.

If an electrode applies stimulation too soon after the intrinsic activation of the heart cells proximate to the electrode, the site is absolutely refractory at this point in time and may not be effected by an additional stimulation pulse. Such unnecessary application of stimulation would waste energy and potentially damage the cells. To overcome such problems, the controller 16 may direct a stimulation pulse to an electrode a preselected time after the last activation was sensed by that electrode, thus, preventing waste of stimulation energy and unnecessary risk of damage to the heart.

The scan may be programmed to follow an approximate spatial path in a tissue which is the same path as the last activation detected by the detector 30, the retrograde direction of the same path, or the direction of the path perpendicular or otherwise angularly positioned to the path of the last activation. The scan may also be sequenced to halt the fibrillation activation fronts without producing new activation fronts. Alternately, scan pacing could be controlled from sensing in the right atrium. This would allow timing of the stimulation to produce summation of stimulation together with the intrinsic activation of the heart pacemaker and conduction system, thus reducing the stimulation energy required and helping to quickly restore a normal rhythmic pattern.

In an alternate embodiment, the temporally distinct pulses may be spaced apart by no less than two milliseconds, although smaller and larger time increments may be utilized. Additionally, a first pulse may be emitted by an electrode, a second pulse being emitted by a different electrode after the beginning of the first pulse and before or concurrent with the ending of the first pulse. Preferably, the beginning of a pulse occurs less than 100 microseconds after the ending of the immediately preceding pulse.

The controller of the present invention is operative to receive a first signal pattern from the sensor or detector. This first signal pattern is indicative of a first heart rhythm, whether such rhythm be normal or abnormal. Next, the controller determines if the therapeutic electrical pulses are to applied to the heart. In the preferred embodiment, the controller sends the received signal pattern to an artificial neural network with back propagation. Such an artificial neural network is operative to recognize a signal pattern which is indicative of an abnormal heart rhythm. It is known in the art that such parallel distributed processing devices process vast amounts of information efficiently. Such artificial neural networks can "learn" to associate a particular input with a given output. In application in the present invention, a signal indicative of a heart rhythm can be input to an artificial neural network which has been "taught" to recognize a signal indicative of an abnormal heart rhythm.

Next, the controller receives, from the artificial neural network, a signal indicating if the received signal pattern is recognized as an abnormal heart rhythm. If the received signal pattern is recognized as an abnormal heart rhythm by the artificial neural network, the artificial neural network sends a signal to the controller indicating that therapeutic electrical pulses are to be applied to the heart. If the artificial neural network does not recognize the received signal pattern as a signal pattern indicative of an abnormal rhythm, the artificial neural network sends a signal to the controller indicating that therapeutic electrical pulses are not to be applied to the heart. The controller is operative to receive these signals from the artificial neural network. If the controller has received a signal from the artificial neural network that the heart rhythm is indicative of an abnormal heart rhythm, the controller is operative to generate a first control signal associated with a first pattern of temporally and spatially separated pulses, and direct the first control signal to the pulse generator. The first control signal is operative to cause the pulse generator to apply the first pattern of temporally and spatially separated pulses to the plurality of electrodes to restore a normal heart rhythm.

If therapeutic pulses are applied to the heart, the controller then receives a second signal pattern from the sensors or detectors, the second signal pattern being indicative of a second heart rhythm. The controller again determines if therapeutic electrical pulses are to be applied to the heart by communicating with an artificial neural network. Alternately, the controller may determine if therapeutic electrical pulses are to be applied to the heart by comparing the received signal pattern with at least one stored pattern indicative of acceptable heart rhythms. If the received signal pattern is comparable to at least one stored pattern indicative of an acceptable heart rhythm, therapeutic electrical pulses are not applied to the heart. Alternately, if the received signal pattern is not comparable to a stored pattern indicative of an acceptable heart rhythm, therapeutic electrical pulses are applied to the heart.

If therapeutic electrical pulses are to be directed to the heart after receipt of the second signal pattern, the controller generates a second control signal associated with a second pattern of temporally and spatially separated pulses and directs the second control signal to the pulse generator to cause the pulse generator to apply the second pattern of temporally and spatially separated pulses to the plurality of electrodes. If therapeutic electrical pulses are not to be applied to the heart after receipt of the second signal pattern from the sensors, the controller is configured to store the second control signal in association with the second received signal pattern. Thus, the system of the present invention stores which sequence was effective in terminating a particular heart rhythm.

The electrodes may be activated individually, in pairs or in groups. If four electrodes are activated in pairs, the first and third electrodes may be paired while the second and fourth electrodes are paired. In an embodiment utilizing six electrodes, the first and fourth electrodes may be paired, the second and fifth electrodes may be paired and the third and sixth electrodes may be paired. Thus, a pair of pulses may be transmitted to the heart through the first and fourth electrodes at a time T1, such energy pulses having the same or opposite polarities. At a time T2, subsequent to the first pair of pulses, another pair of pulses are emitted through a second and fifth electrodes. Likewise, a third pair of pulses are emitted through the third and sixth electrodes at a time T3 subsequent to the previous two pairs of pulses.

An almost limitless number of scan sequences may be designed to be applied through the spaced apart electrodes. FIGS. 3–5 graphically depict a variety of scan stimulation patterns which may be applied through six electrodes. As shown in FIG. 3, a scan sequence is depicted wherein a pulse is emitted through each electrode sequentially. At time T1, a first pulse is emitted through electrode 1, and a second pulse is emitted through electrode 2 at time T2. Likewise, a third pulse is emitted through electrode 3 at time T3, a fourth pulse is emitted through electrode 4 at T4, a fifth pulse is emitted through electrode 5 at T5, and a sixth pulse is emitted through electrode 6 at T6. As shown in FIG. 3, each pulse has the same polarity. FIG. 4 depicts an alternate pattern wherein electrodes 1 and 4 are paired, electrodes 2 and 5 are paired, and electrodes 3 and 6 are paired. At time T1, electrodes 1 and 4 emit a positive pulse. At time T2, electrodes 2 and 5 emit a positive pulse and, at time T3, electrodes 3 and 6 emit positive pulses. At time T4, electrodes 1 and 4 emit a negative pulse to the heart, at time T5 electrodes 2 and 5 emit a negative pulse to the heart and, at time T6, electrodes 3 and 6 emit negative pulses to the heart.

In a scan sequence depicted in FIG. 5, electrode 1 emits, at T1, a positive pulse while electrode 4 simultaneously emits a negative pulse. At time T2, electrode 2 emits a positive pulse and electrode 5 emits a negative pulse. At time T3, electrode 3 emits a positive pulse while electrode 6 emits a simultaneous pulse which is negative. At time T4, electrode 1 emits a negative pulse and electrode 4 emits a positive pulse. At time T5, electrode 2 emits a negative pulse and electrode 5 emits a positive pulse. At time T6, electrode 3 emits a negative pulse and electrode 6 emits a positive pulse. A seemingly infinite variety of scan stimulation sequences may be created depending on the number of electrodes selected and the polarity and sequence of pulsing of such electrodes.

In a preferred embodiment a first pulse beginning at time T1 and ending at time T3 is emitted. A second pulse, beginning at time T2, is emitted after T1 but before T3. Alternately, the second pulse may begin at time T3, the beginning of the second pulse occurring simultaneously with the ending of the first pulse.

Having described the various embodiments of the present invention with reference to the accompanying figures, it will be appreciated that various changes and modifications can be made without departing from the scope or spirit of the invention.

I claim:

1. A method for applying therapeutic electrical pulses to the heart comprising the steps of:

providing a plurality of spaced-apart electrodes, each electrode in electrical communication with a heart fiber adjacent to the electrode;

directing a sequence of spatially and temporally distinct anti-tachyarrhythmia pulses to the heart wherein the sequence comprises a first pulse to the heart through a first electrode at a time T1, a second pulse to the heart through a second electrode at a time T2, occurring at least two milliseconds after T1.

2. The method of claim 1 wherein the step of providing a plurality of electrodes includes the step of providing a plurality of elongated electrodes, at least one electrode extending substantially parallel to an elongated fiber of the heart proximate to such electrode.

3. The method of claim 1 further including the step of detecting an abnormal heart rhythm.

4. The method of claim 1 wherein the step of providing a plurality of electrodes includes the step of providing at least four electrodes.

5. A method for applying therapeutic electrical pulses to the heart comprising the steps of:

providing a plurality of electrodes, each electrode in electrical communication with a heart fiber adjacent to such electrode;

providing a pulse generator which generates anti-tachyarrhythmia energy pulses;

detecting an abnormal heart rhythm;

directing a first pulse to the heart through a first electrode at a time T1; and directing a second pulse to the heart through a second electrode at a time T2, T2 occurring at least two milliseconds after T1.

6. The method of claim 5 further comprising the steps of:

directing a third pulse to the heart through a third electrode at time T3, T3 being later in time than T2;

directing a fourth pulse to the heart through a fourth electrode at time T4, T4 being later in time than T3;

directing a fifth pulse to the heart through a fifth electrode at time T5, T5 being later in time than T4; and directing a sixth pulse to the heart through a sixth electrode at time T6, T6 being later in time than T5.

7. The method of claim 5 further including the steps of:

directing a third pulse to the heart through a third electrode at time T1; and directing a fourth pulse to the heart through a fourth electrode at time T2.

8. The method of claim 7 wherein directing said first and third pulses includes directing pulses having the same polarity.

9. The method of claim 7 wherein directing said first and third pulses includes directing pulses having opposite polarity.

10. The method of claim 5 further including the steps of:

directing a third pulse to the heart through a third electrode at time T3, T3 being later in time than T2;

directing a fourth pulse to the heart through a fourth electrode at time T1;

directing a fifth pulse to the heart through a fifth electrode at time T2; and directing a sixth pulse to the heart through a sixth electrode at time T3.

11. The method of claim 5 wherein the step of providing a plurality of electrodes includes the step of providing a plurality of elongated electrodes, at least one electrode extending substantially parallel to an elongated fiber of the heart proximate to such electrode.

12. The method of claim 5 further including the step of storing the sequence of spatially and temporally applied pulses directed to the heart.

13. A system for applying therapeutic electrical pulses to the heart comprising:

a power source;

a controller in electrical communication with the power source;

pulse means in electrical communication with the controller and power source, the pulse means configured to generate a sequence of energy pulses;

a plurality of spaced apart elongated electrodes, each electrode in electrical communication with the pulse means, each electrode configured to deliver at least one of the energy pulses generated by the pulse means to a patient's heart; and detecting means in electrical communication with the controller, the detecting means operative to detect an abnormal rhythmic condition in the patient's heart and transmit a signal to the controller to indicate an abnormal rhythmic condition, the controller being operative to receive the signal indicative of an abnormal rhythmic condition and to cause the pulse means to direct a sequence of spatially and temporally distinct pulses to the patient's heart through the electrodes, each pulse passing through at least one of the electrodes.

14. The system of claim 13 comprising at least four electrodes.

15. The system of claim 13 wherein each of the plurality of spatially and temporally distinct pulses has a beginning and an ending, the beginning of each pulse being spaced apart from the beginning of the immediately preceding pulse.

16. The system of claim 15 wherein the beginning of each pulse is spaced apart from the ending of the immediately preceding pulse by no more than 100 microseconds.

17. The system of claim 13 further including memory means in electrical communication with the controller.

18. The system of claim 17 wherein the memory means is configured to store at least two different sequences of spatially and temporally distinct pulses.

19. The system of claim 18 wherein each stored sequence of spatially and temporally distinct pulses is associated with an indicator, also stored in memory, which associates the sequence of pulses with at least one type of abnormal rhythmic condition detectable by the detecting means.

20. The system of claim 13 wherein the controller is further operative to direct a first sequence of spatially and temporally distinct pulses to the heart and, if the detecting means transmits a signal indicative of an abnormal rhythmic condition in the patient's heart to the controller after application of the first sequence of pulses, the controller being further operative to direct a second sequence of pulses to the heart.

21. The system of claim 20 wherein the second sequence of pulses differs from the first sequence of pulses.

22. The system of claim 13 wherein the electrodes are operative to detect electrical activation of heart fibers proximate to each such electrode.

23. A system for applying therapeutic electrical pulses to a heart comprising:
   I. a plurality of spaced apart electrodes configured to be disposed in contact with a heart;
   II. sensor means configured to be disposed in contact with the heart;
   III. a pulse generator in electrical communication with the plurality of electrodes, the pulse generator being operative to apply a pattern of temporally and spatially separated pulses to the heart through the plurality of electrodes;
   IV. a controller in electrical communication with the plurality of electrodes, the sensor means and the pulse generator, the controller performing the steps of:
      a. receiving a first signal pattern from the sensor means, the first signal pattern being indicative of a first heart rhythm;
      b. determining if therapeutic electrical pulses are to be applied to the heart;
   if therapeutic electrical pulses are to be applied to the heart,
      c. generating a first control signal;
      d. directing the first control signal to the pulse generator to cause the pulse generator to apply a first pattern of temporally and spatially separated pulses to the plurality of electrodes;
      e. receiving a second signal pattern from the sensor means, the second signal pattern being indicative of a second heart rhythm;
      f. determining if therapeutic electrical pulses are to be applied to the heart;
   if therapeutic electrical pulses are to be applied to the heart,
      g. generating a second control signal;
      h. directing the second control signal to the pulse generator to cause the pulse generator to apply a second pattern of temporally and spatially separated pulses to the plurality of electrodes; and
   if therapeutic electrical pulses are not to be applied to the heart,
      i. storing the second control signal in association with the second signal pattern.

24. The system claimed 23 wherein the steps of determining if therapeutic electrical pulses are to be applied to the heart includes the steps of:
   sending the received signal pattern from the controller to an artificial neural network configured to recognize a signal pattern indicative of an abnormal heart rhythm; and
   the controller then receiving from the artificial neural network a signal indicating if therapeutic electrical pulses are to be directed to the heart.

25. The system claimed in claim 23 wherein the steps of determining if therapeutic electrical pulses are to be directed to the heart include the steps of:
   the artificial neural network comparing the received signal pattern with at least one stored pattern indicative of acceptable heart rhythms;
   if the received signal pattern is comparable to at least one stored pattern indicative of an acceptable heart rhythm, therapeutic electrical pulses are not to be directed to the heart; and
   if the received signal pattern is not comparable to at least one stored pattern indicative of an acceptable heart rhythm, therapeutic electrical pulses are to be directed to the heart.

26. A method for applying therapeutic electrical pulses to the heart comprising the steps of:
   providing a plurality of spaced apart electrodes configured to be disposed in contact with a heart;
   providing sensor means configured to be disposed in contact with the heart;
   providing a pulse generator in electrical communication with the plurality of electrodes and sensor means, the pulse generator being operative to apply a pattern of temporally and spatially separated pulses to the heart through the plurality of electrodes;
   receiving a first signal pattern from the sensor means, the first signal pattern being indicative of a first heart rhythm;
   determining if therapeutic electrical pulses are to be applied to the heart;
   storing the first control signal in association with the first signal pattern;
   if therapeutic electrical pulses are to be applied to the heart, generating a first control signal;
   directing the first control signal to the pulse generator to cause the pulse generator to apply a first pattern of temporally and spatially separated pulses through the plurality of electrodes;
   receiving a second signal pattern from the sensor means, the second signal pattern being indicative of a second heart rhythm;
   determining if therapeutic electrical pulses are to be applied to the heart;
   and if therapeutic electrical pulses are to be applied to the heart, generating a second control signal directing the second control signal to the pulse generator to cause the pulse generator to direct a second pattern of temporally and spatially separated pattern of pulses to the plurality of electrodes; and
   if therapeutic electrical pulses are not to be applied to the heart, storing the second control signal in association with the second signal pattern.

27. A method for applying therapeutic electrical pulses to the heart comprising the steps of:
   providing a plurality of electrodes, each electrode in electrical communication with a heart fiber adjacent to such electrode;
   providing a pulse generator which generates energy pulses;
   detecting an abnormal heart rhythm;
   directing a first pulse to the heart through a first electrode at a time T1;
   directing a second pulse to the heart through a second electrode at a time T2, T2 being later in time than T1;

directing a third pulse to the heart through a third electrode at a time T3, T3 being later in time than T2;

directing a fourth pulse to the heart through a fourth electrode at a time T4, T4 being later in time than T3;

directing a fifth pulse to the heart through a fifth electrode at a time T5, T5 being later in time than T4; and directing a sixth pulse to the heart through a sixth electrode at a time T6, T6 being later in time than T5.

28. A method for applying therapeutic electrical pulses to the heart comprising the steps of:

providing a plurality of electrodes, each electrode in electrical communication with a heart fiber adjacent to such electrodes;

providing a pulse generator which generates energy pulses;

detecting an abnormal heart rhythm;

directing a first pulse to the heart through a first electrode at a time T1;

directing a second pulse to the heart through a second electrode at a time T2, T2 being later in time than T1;

directing a third pulse to the heart through a third electrode at a time T1; and directing a fourth pulse to the heart through a fourth electrode at a time T2.

* * * * *

UNITED STATES PATENT AND TRADEMARK OFFICE
CERTIFICATE OF CORRECTION

PATENT NO. : 5,995,871

DATED : November 30, 1999

INVENTOR(S) : Stephen B. Kaisley

It is certified that error appears in the above-identified patent and that said Letters Patent is hereby corrected as shown below:

On the Title Page, Other Publications - In the "Saypol, J.; Roth B.' 'Mechanism for Anistropic Reentry in Electrically Active Tissue.' " Delete "Biomedical Engineering and Instrumentation Program, National Center for Reserch Resources, Nat'l Institute of Health, Bethesda, Maryland" and insert --J Cardiovasc Eletrophysiol, Vol. 3, pp. 558-566 (Dec. 1992)--

On the Title Page Other Publications - In the "Knisley S., 'Transmembrabe Voltage Changes During Unipolar Stimulation of Rabbit Ventricle.' " Delete "Div. of Cariovascular Disease of the School of Medicine and Dept. of Biomedical Engineering, University of Alabama Birmingham. accepted Aug. 27, 1995" and insert --Circ Res. 1995; 77; 1229 - 1239 --

Page 2, Other References - In the last publication reference, Delete "Biomedical Engineering Center, Purdue University, West Lafayette, Indiana and Medtroic, Inc., Minneapolis, Minnesota" and insert --Medical Instrumentation Vol. 20, No.3, May - June 1986--

Column 4, line 17 - Before "drawing" insert --the--
Column 4, line 67 - Replace "heart 12" with --catheter 26--
Column 6, line 60 - Replace "effected" with --affected--
Column 7, line 29 - After "to" insert --be-- (second occurrence)
Coulmn 11, line 15 - Replace "system" with --method--
Coulmn 11, line 16 - Before "comprising" insert --a system--
Column 11, line 58 - After "claimed" insert --in claim--
Column 12, line 32-33 - Move contents of lines "32-33" and insert after line --35--

Signed and Sealed this

Tenth Day of April, 2001

*Attest:*

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 5,995,871
DATED : November 30, 1999
INVENTOR(S) : Stephen B. Knisley It is certified that error appears in the above-identified patent and that said Letters Patent is hereby corrected as shown below:

Column 1,
Line 4, insert:

-- GRANT REFERENCE

The subject invention was made with government support under a grant from the National Institutes of Health, Grant No. HL52003. The government has certain rights in the invention. --.

Signed and Sealed this

Twenty-fourth Day of January, 2006

JON W. DUDAS
*Director of the United States Patent and Trademark Office*